(12) United States Patent
LeMahieu

(10) Patent No.: US 6,757,413 B1
(45) Date of Patent: Jun. 29, 2004

(54) LOW-COST MEDICAL IMAGE TRANSFER AND CONTROL SYSTEM AND METHOD

(75) Inventor: Edward LeMahieu, Minneapolis, MN (US)

(73) Assignee: American TeleCare, Inc., Eden Prairie, MN (US)

( * ) Notice: Subject to any disclaimer, the term of this patent is extended or adjusted under 35 U.S.C. 154(b) by 0 days.

(21) Appl. No.: 09/511,576

(22) Filed: Feb. 23, 2000

(51) Int. Cl.[7] .............................................. G06K 9/00
(52) U.S. Cl. .................. 382/128; 382/232; 379/106.02; 600/301
(58) Field of Search .............................. 382/128, 232; 348/14.12, 14.13; 379/106.01, 106.02; 600/301

(56) References Cited

U.S. PATENT DOCUMENTS

| | | | |
|---|---|---|---|
| 4,261,344 A | 4/1981 | Moore et al. ................... 128/6 |
| 4,854,302 A | 8/1989 | Allred, III ..................... 128/6 |
| 5,239,984 A | 8/1993 | Cane et al. ..................... 128/9 |
| 5,333,063 A | 7/1994 | Yoo ........................... 358/448 |
| 5,363,839 A | 11/1994 | Lankford ...................... 128/9 |
| 5,384,643 A | 1/1995 | Inga et al. .................... 358/403 |
| 5,416,602 A | 5/1995 | Inga et al. .................... 358/403 |
| 5,441,047 A | 8/1995 | David et al. ................. 128/670 |
| 5,453,786 A | 9/1995 | Trent ........................... 348/384 |
| 5,527,261 A | 6/1996 | Monroe et al. ............. 600/109 |
| 5,539,452 A | 7/1996 | Bush et al. ................... 348/17 |
| 5,544,649 A | 8/1996 | David et al. ................. 128/630 |
| 5,563,649 A | 10/1996 | Gould et al. ................. 348/17 |
| 5,568,185 A | 10/1996 | Yoshikazu .................... 348/22 |
| 5,640,953 A | 6/1997 | Bishop et al. .............. 128/630 |
| 5,662,586 A | 9/1997 | Monroe et al. ............. 600/110 |
| 5,682,199 A | 10/1997 | Lankford ..................... 348/72 |
| 5,699,458 A * | 12/1997 | Sprague ....................... 382/250 |
| 5,704,364 A | 1/1998 | Saltzstein et al. ........... 128/696 |
| 5,762,605 A | 6/1998 | Cane et al. .................. 600/200 |
| 5,800,344 A | 9/1998 | Wood, Sr. et al. .......... 600/188 |
| 5,806,005 A | 9/1998 | Hull et al. ................... 455/566 |
| 5,885,214 A | 3/1999 | Monroe et al. ............. 600/407 |
| 5,907,604 A * | 5/1999 | Hsu ....................... 379/142.06 |
| 5,917,429 A | 6/1999 | Otis, Jr. et al. ......... 340/870.31 |
| 5,919,130 A | 7/1999 | Monroe et al. ............. 600/200 |
| 5,931,791 A | 8/1999 | Saltzstein et al. ........... 600/513 |
| 5,941,829 A | 8/1999 | Saltzstein et al. ........... 600/509 |
| 5,982,420 A * | 11/1999 | Ratz ............................ 348/171 |
| 6,014,432 A * | 1/2000 | Modney ................ 379/106.02 |
| 6,323,892 B1 * | 11/2001 | Mihara .................... 348/14.01 |
| 6,522,418 B2 * | 2/2003 | Yokomizo et al. .......... 358/1.15 |

OTHER PUBLICATIONS

Cheng et al. "Electronics Development of Silicon Microdisplay for Virtual Reality Applications", Jan. 18, 1999–Jan. 21, 1999, Proceedings of the ASP–DAC '99, pp. 197–200.*

* cited by examiner

Primary Examiner—Leo Boudreau
Assistant Examiner—Ryan J. Miller
(74) Attorney, Agent, or Firm—Patterson, Thuente, Skaar & Christensen, P.A.

(57) ABSTRACT

A medical image transfer and control system of the present invention preferably utilizes a medical image snap-shot formatting device. This device generally includes a digital signal processor and a signal formatting component that is operably connected to the digital signal processor. The signal formatting component is designed to receive medical image snap-shot data from a camera and, if necessary, format the data to a digital format. The signal formatting component then forwards the digital data to the digital signal processor which operates to compress the data to a format suitable for transfer over a plain old telephone system (POTS).

8 Claims, 2 Drawing Sheets

LOW-COST MEDICAL IMAGE TRANSFER AND CONTROL SYSTEM AND METHOD

FIELD OF THE INVENTION

The present invention relates to medical image transfer and control between a patient and a healthcare professional and, more particularly, to a high-resolution video snapshot capability that is integrated with a medical image transfer and control system that utilizes standard telephone lines and that accommodates a plurality of patient-used digital camera types while still providing the patient a substantially low-cost system.

BACKGROUND OF THE INVENTION

Telemedicine home care providers equip patients with a monitoring unit that is placed in the patients home and connected to the home care nurse or other health care provider via the patient's existing telephone line. The monitoring unit typically allows voice, video, and data interaction between the patient and the nurse according to an H.324 standard. H.324 is defined as an International Telecommunications Union standard that provides point-to-point data, video, and audioconferencing over analog telephone lines (POTS) at a data transmission rate of 48 Kbps, however, in practice data transmission can occur at rates up to 2048 megabits per second. The monitoring unit provides for the ability transfer various medical data such as heart sounds, blood pressure, blood glucose, pulse oximetry, spirometry, and other data. The name sometimes applied to this complex set of activities is telehomecare.

In certain areas of the medical monitoring of a patient it is important or, in some cases crucial, that a telehomecare patient be able to transfer to the monitoring medical professional a high-resolution video snapshot. This is especially important in wound care management where the color and appearance of a wound must be discernable for an accurate diagnosis to be made and/or medical follow-up to occur.

Generally, all of the current telehomecare systems that provide patient users with a high resolution video snapshot capability require that the patient utilize a personal computer (PC) that has been equipped with a compatible video capture card to interface with various types of cameras. These systems are complex and, because they are PC-based, quite expensive due to the advanced electronic hardware that is used within the PC platform. These PC-based telehomecare systems, while technically advanced, often provide a telehomecare user with features that are too complicated to use or are simply unnecessary.

Those telehomecare systems that are not PC-based simply do not provide the user with a high-resolution video snapshot capability. Rather, the user is provided only with video snapshots that are low resolution and poor in color. The low resolution and poor color are due largely to the limitations of bandwidth in real time data transfer over telephone lines, i.e., the H.324 standard.

As such, there is a need for a medical image transfer system that provides the patient user with an in-home device that is capable of handling a number of medical devices, including various types of digital cameras, capable of providing high-resolution video snapshot capability over standard telephone lines while still providing a low-cost system to the user.

SUMMARY OF THE INVENTION

The needs described above are in large measure met by the low-cost medical image transfer and control system of the present invention. The medical image transfer and control system achieves its low cost by utilizing a non-PC based system and achieves its high-resolution snapshot capability by giving up real time video data transfer in favor of delayed video transfer.

The medical image transfer and control system of the present invention preferably utilizes a medical image snapshot formatting device. This device generally includes a digital signal processor and a signal formatting component that is operably connected to the digital signal processor. The signal formatting component, e.g., controller or decoder, is designed to receive medical image snap-shot data from a camera and, if necessary, format the data to a digital format. The signal formatting component then forwards the digital data to the digital signal processor which operates to compress the data to a format suitable for transfer over a plain old telephone system (POTS).

The medical image snap-shot formatting device is designed so that it may be implemented within a new or existing patient system of a telemedicine system. The patient system preferably includes one or more cameras, for taking medical images, which are interfaced to the medical image snap shot formatting device. Within the patient system, the digital signal processor of the formatting device is operably connected to a second digital signal processor that generally performs the non-video functions for the patient system. The compressed medical image data produced by the digital signal processor of the formatting device is preferably passed through the second digital signal processor and out over the POTS to a medical professional system for viewing.

The formatting device may additionally include a second signal formatting component that format the medical image snap-shot data to a format suitable for use by a video monitor, which preferably forms part of the patient system. The patient system may additionally include various non-camera, medical peripherals such as a blood pressure meter, pulse meter, glucose monitor, a stethoscope, etc. The digital signal processor of the formatting device utilizes a compression algorithm which defines a compression loss percentage. Both the algorithm and the loss percentage may be adjusted remotely, over the POTS, through use of the medical professional system.

DESCRIPTION OF THE PREFERRED EMBODIMENTS

Figure 1:
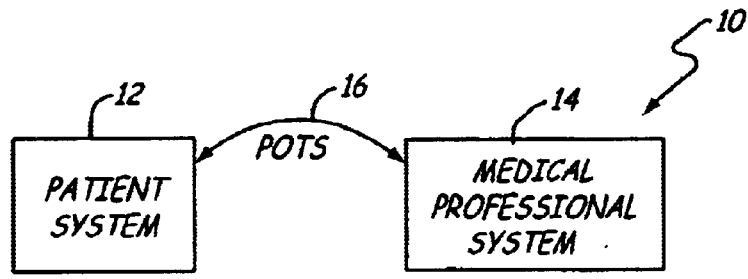
FIG. 1 provides a system overview of the low-cost medical image transfer and control system/method of the present invention.

The present invention comprises a medical image transfer and control system 10 that is for use in the telemedicine industry. Referring to FIG. 1, system 10 generally comprises a patient system 12 that is operably connected to a medical professional system 14 via a telephone communication 16, i.e., POTS. Patient system 12 is described in further detail in the paragraphs below. Medical professional system 14 preferably comprises a PC-based monitoring system that is configured to transmit and receive data, including video and voice data. The preferred medical professional system 14 is the Aviva Central Telemedicine Station (CTS) available from American Telecare, Inc. of Eden Prairie, Minn. The use and operation of the CTS are described in the installation and operations manual for the CTS, i.e., Aviva SLX System (American Telecare, Dec. 1999),which is hereby incorporated by reference. Medical professional system 14 is typically located in a traditional medical setting, e.g., clinic, hospital, nursing home, etc.

Figure 2:
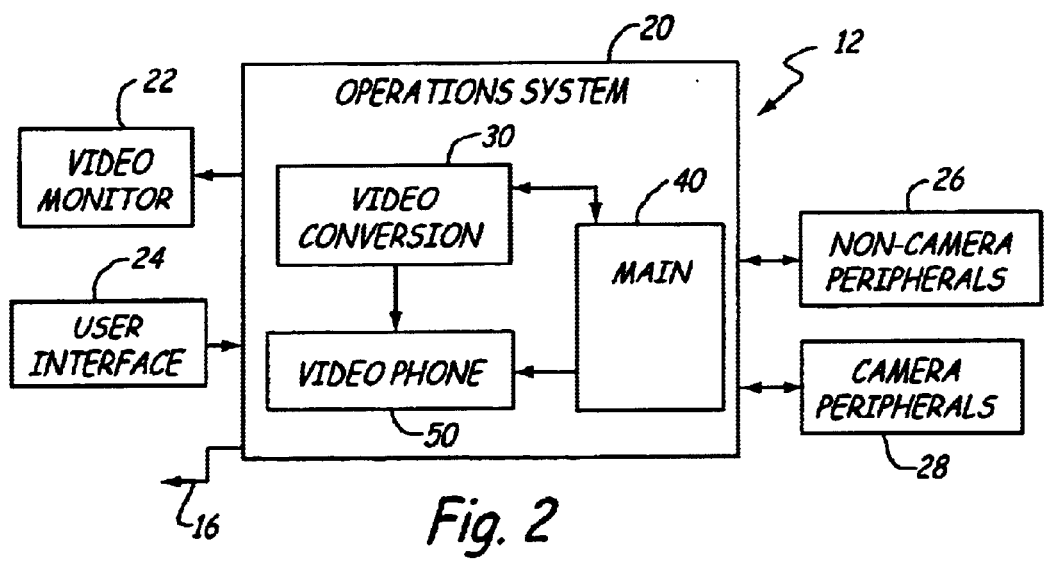
FIG. 2 provides a block diagram of a patient system that is depicted in the system overview of FIG. 1.

A block diagram overview of patient system 12 is provided in FIG. 2. As shown, patient system 12 generally comprises an operations system 20, a standard video monitor 22, a user interface 24 (which is preferably a single pushbutton the depression of which allows the user to answer a call from medical professional system 14), one or more non-camera medical peripherals 26, and one or more camera medical peripherals 28. Patient system 12 is typically located in a non-traditional medical setting, e.g., a patient's home or workplace.

Operations system 20, as depicted in FIG. 2, generally includes the components of a video conversion board 30, a main board 40, and a videophone board 50. Note that each of boards 30, 40, and 50 may exist as separate boards or may be combined on one or more boards without departing from the spirit or scope of the invention.

Non-camera peripherals 26 of patient system 12 generally include such items as a blood pressure meter, pulse meter, glucose monitor, and/or a stethoscope. Of course, other non-camera peripherals 26 may be used without departing from the spirit or scope of the invention. Camera peripherals 28 of patient system 12 preferably include one or more of the following digital or analog output cameras, which may or may not be incorporated within a medical instrument, see FIG. 3: (1) a universal serial bus (USB) camera, 281; (2) a camera with S-video output, 282; and/or (3) a composite video camera 283, e.g., a national television system committee (NTSC) camera, phase alternate line (PAL) camera, sequential couleur avec memoire (SECAM) or a standard camcorder. Note that each of these cameras may be provided with the ability to allow the user to adjust focus, lighting, location, and/or aiming of the camera. Further, while camera peripherals 28 may be used for any desired purpose without departing from the spirit or scope of the invention, in the present invention, they are typically used to capture the image of a patient's face, the image of a wound, or the image of a pill bottle.

Figure 3:
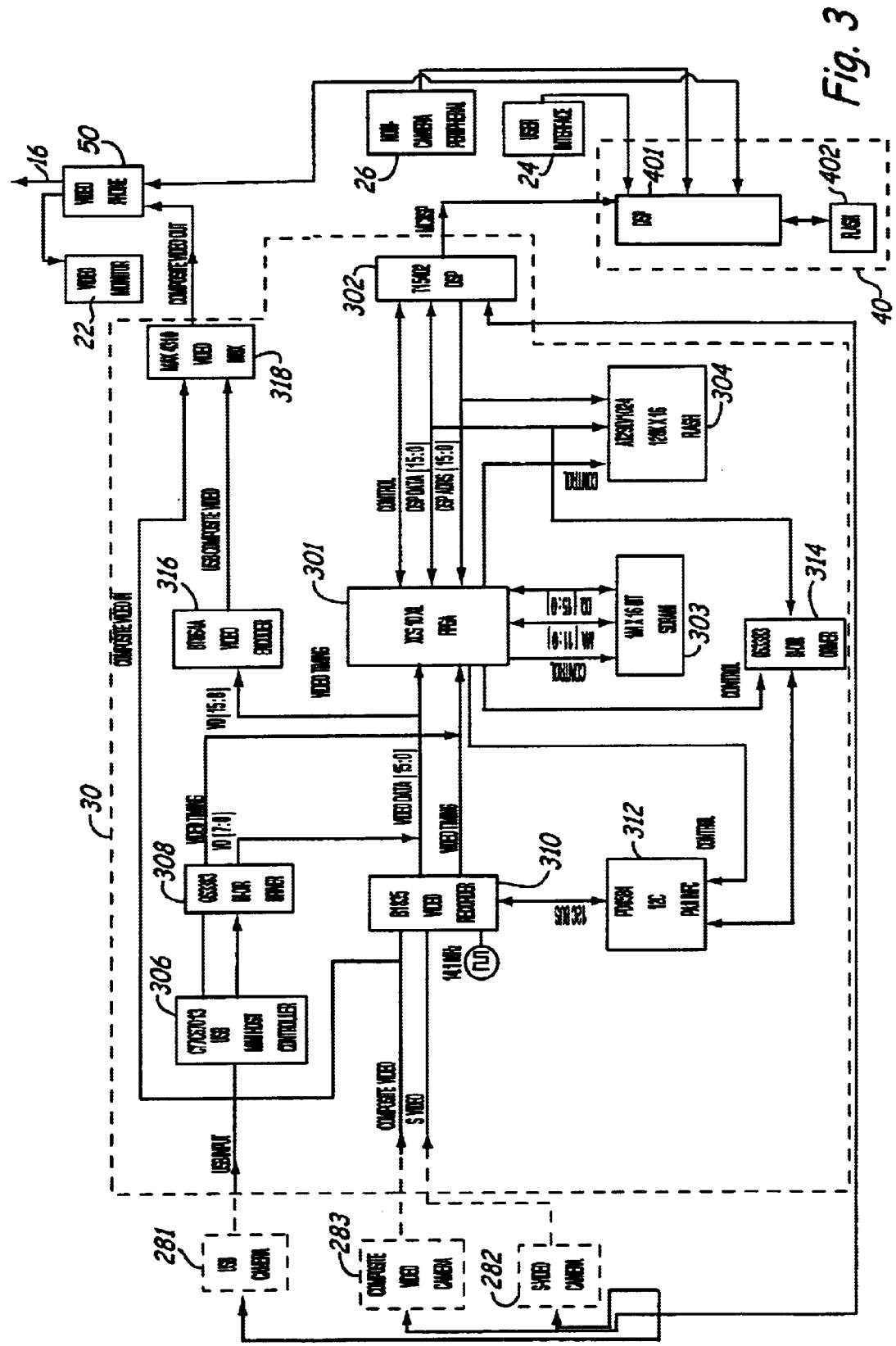
FIG. 3 provides a block diagram of an operations system and peripherals that are depicted in the block diagram of FIG. 2.

Referring now to FIG. 3, patient system 12 and, more particularly, operations system 20 is depicted in detail. Moving from left to right on FIG. 3, patient system 12 preferably incorporates one or more USB cameras 281, S-video cameras 282, and/or composite video camera 283 that are directly interfaced to video board 30.

Video board 30 preferably includes a video glue logic field programmable gate array (FPGA) 301, a digital signal processor (DSP) 302, a synchronous dynamic random access memory (SDRAM) 303, a flash memory EPROM 304 providing non-volatile memory for program storage, and various components for the receipt and formatting of the various camera output signals. Note that DRAM, as opposed to static access memory (SRAM), is selected for the low-cost benefit it provides, however, any suitable type of RAM may be used without departing from the spirit or scope of the invention. As indicated by the arrows between components, control of video board 30 is shared between DSP 302 and FPGA 301 under the direction of the program within flash EPROM 304.

The various components for the receipt and formatting of the various camera output signals include a USB mini-host controller 306 that converts the USB output signal from camera 281 to a digital signal that is transmitted through a bi-directional driver 308. Bi-directional driver 308 operates as an interface between logic levels, e.g., between 5 volt and 3 volt logic, to create compatibility. The various components further include a video decoder 310 that operates to convert composite video and S-video to a digital signal. Video decoder 310 is under the control of FPGA 301 via I2C interface 312. Further, a second bi-directional driver 314 operates as an interface between DSP 302 and I2C interface 312. The various components also include a video encoder 316 that converts a digital video stream, i.e., YCrCb digital video, to a composite video stream. This composite video stream is provided to a video multiplexor (MUX) 318 that provides for switching between at least two digital video streams, i.e., the digital video stream generated by video encoder 316 and the digital video stream generated directly by camera 283. The output of MUX 318 is provided to video phone board 50 of operations systems 20.

Main board 40 of operations system 20 is preferably provided with a digital signal processor (DSP) 401 as well as a flash memory EPROM 402 for program storage. DSP 401 is connected to DSP 302 via a high speed serial bus and as well to video phone board 50 via a proprietary communications protocol established by the manufacturer of the video phone board 50. In communicating with videophone board 50, DSP 401 operates as a speakerphone. Further, DSP 401 is directly interfaced to non-camera peripherals 26.

Videophone board 50 is preferably an H324 compatible videophone and, more preferably, a ViaTVPhone model VC55 or VMK5 as manufactured by 8x8 Inc. The ViaTV-Phone has a bandwidth of approximately 3K for digital audio data, approximately 20K for digital image data, and typically 9.6K for other data sent via asynchronous data port. Of course, other videophone boards 50, and other divisions of available bandwidth, may be used without departing from the spirit of scope of the invention.

In operation, system 10 preferably performs as follows. Medical professional station 14 places a call to patient station 12 via telephone line, POTS 16. The patient residing proximate patient station 12 utilizes user interface 24 to answer the incoming call, e.g., the patient depresses a button to receive the call. The activation of user interface 24 sends a signal to DSP 401 which, in turn, directs video phone 50 to establish the call. Once the call is established the patient and medical professional initially interact via audio communication. DSP 401 operates as the speaker phone transmitting and receiving audio through speaker phone board 50.

Upon the patient receiving the direction from the medical professional, the patient preferably positions one or more of camera peripherals 28 for the taking of a video image snap-shot of a desired feature and awaits a "take snap-shot" command from medical professional system 14. Upon issuance of the "take snap-shot" command from medical professional system 14, the command is transferred to DSP 401 of patient system 12 and then to DSP302 whereby the operation of one or more camera peripherals 28 is initiated and the image taken. The video image snap-shot is then converted by controller 306, decoder 310 and/or encoder 316, as required, and directed along the appropriate paths, see FIG. 3. A digital data stream, occurring as a sequence of digital video pixel data (one frame), representative of the video image snap-shot taken by the patient is provided to FPGA 301 while an NTSC data stream, created by encoder 316, is provided via MUX 318 to videophone 50 for display to the patient.

Once the snap-shot image has been taken, medical professional system 14 provides a signal to DSP 401 to transfer the snap-shot video image to medical professional system 14. DSP 401 transfers this request to DSP 302 which, in turn relays the request to FPGA 301. FPGA 301 then operates to synchronize to the digital video frames and to deposit the digital data of at least one of the video frames into memory, SDRAM 303. Upon completing the deposit of the video frame into memory, FPGA 301 signals DSP 302 and provides its output thereto.

Upon receiving the output from FPGA 301, DSP 302 operates to compress the data in a JPEG format so that it is ready to transport over a low bit rate data channels over POTS 16. It should be noted that while JPEG is the preferred compression format other compression formats, e.g., wavelets, etc., may be used without departing from the spirit or scope of the invention. JPEG format allows for the specification of a quality level, i.e. percent of loss or even loss-less compression. A snapshot, i.e., a digital video frame, with low percent loss or loss-less compression provides an image quality that is significantly higher than that currently available with real time image transfer. The use of the snapshot digitized image herein results in slower image transfer, compared with real time transfer, however, significantly higher quality of the image is provided in terms of resolution and color depth.

Once DSP 302 has operated to compress the video image, the compressed video image data is transferred from DSP 302 via high speed serial bus to DSP 401. DSP 401 then provides the compressed video image data, as directed by the program residing within flash EPROM 401, to videophone board 50 where it is transferred out to medical professional system 14 over POTS 16. Upon receiving the video image data, medical professional system 14 operates to decompress the data for viewing of the snap-shot image. The image data may be color and/or light corrected to enhance the viewed image.

Because the transfer of a high-resolution, snap-shot video image from patient system 12 to medical professional system 14 is a rather slow process, e.g., a 25 KByte file takes approximately one minute (typical images are 10 to 20 KBytes but could be as much as 30 to 40 KBytes), patient system 12 is preferably configured to first supply medical professional system 14 with a "thumbnail" image, i.e., an image of significantly lower quality (e.g. lower quality resolution, color depth, and/or display size), upon receiving the signal to transfer the image. The "thumbnail" image may generally be transferred within approximately five seconds allowing the medical professional to determine if the image is correct without having to endure the longer wait of the transfer of the high resolution image. The procedure by which the thumbnail image is transferred to medical professional system 14 is the same as that described for the high-resolution snap-shot image, however, DSP 302 is provided with coding to compress the "thumbnail" image data to approximately 99+%. If the "thumbnail" image is correct, the medical professional may then request the high-resolution snap-shot image as described above. Alternatively, the medical professional may request yet another image at an intermediate compression/quality level and then request the high-resolution snap-shot image. The rate of compression of the image is generally in the range of 90 to 99+% and is altered/adjusted per the resolution desired and the application at hand. For instance, a compression percentage of 96–97% generally offers the most optimal price/performance ratio for wound-care applications.

As such, the medical professional, while not provided with a real-time image, is provided with a high-resolution snap-shot of a feature of interest. Further, the patient is provided with a convenient and low-cost manner of providing that snap-shot image. Specifically, because the functions to be performed within patient system 12 are distributed between DSP 302, performance of video conversion functions, and DSP 401, performance of non-video conversion functions, rather than relying on an expensive PC-base processor, operating system and supporting circuitry, significant cost-reduction is provided to patient system 12. This distributed approach also allows for an accessory product concept patient system 12 in that a patient is now provided with the option of including or omitting video board 30 from operations system 20 as needed or desired without alteration of main board 40 or videophone board 50.

If snap-shot image ability is desired, the option of additional cost-reduction is provided to the patient by virtue of the availability of multiple camera interface options. The availability of multiple camera interface options allows flexibility of cost and image quality that can be tailored to meet the requirements of a given patient situation. The use of a higher resolution but higher cost video camera may be utilized for situations requiring greater detail. However, the option of using lower cost equipment remains for those situations where less detail is required.

While not required for operation, operations system 20 of patient system 12 is preferably provided with the ability for remote adjustment. Specifically, operations system 20 is preferably provided with the ability for remote adjustment of the loss percentage that is to be applied upon compression the snap-shot video image. The loss percentage remote adjustment is preferably achieved by the medical professional entering a loss percentage/quality level setting at medical professional system 14 then downloading, via POTS 16, the setting to patient system 12. Alternatively, the medical professional may enter a new snap-shot video image compression algorithm, e.g., one provided as a software update, and then download the algorithm to patient system 12. Upon reaching patient system 12, the setting and/or algorithm is transmitted from videophone board 50 to DSP 401 of main board 40. DSP 401 then transfers the setting and/or algorithm to DSP 302 where it is then programmed into flash memory, EPROM 304.

Camera peripherals 28 of patient system 12 are also preferably provided with the ability for remote adjustment. Specifically, focus, lighting, and other directions for adjustment of the settings of the various camera peripherals 28 are preferably entered at medical professional system 14 then transferred via POTS 16 through videophone board 50 of patient system 12 to DPS 401 of main board 40. DSP 401 then relays the command to DSP 302 which in turn controls the settings of the various camera peripherals 28 via a direct connection to camera peripherals 28. Alternatively, control of camera peripherals 28 may be directed via FPGA 301.

While the description of the operation of system 10 above has been related to the taking and transfer of a snap-shot video image, system 10, and specifically patient system 12, is additionally capable of performing numerous additional functions. These functions are generally performed by main board 40 of operations system 20. The functions include communicating with non-camera peripherals 26, as is known in the art, and transferring the data provided by the non-camera peripherals to medical professional station 14. For example, main board 40 preferably operates as a stethoscope sender, as described in detail in U.S. Pat. Nos. 5,841,846 and 5,550,902 (assigned to American Telecare, Inc.), which are hereby incorporated by reference.

System 10 provides the ability to transfer image data from patient system 12 to medical professional system 14 which allows the medical professional to monitor wound healing, medication dosages, and other visual medical parameters that can be captured in a single snapshot video image frame. This image transfer ability along with the ability to transfer medical data and that of verbal communication provides for fully rounded in-home medical monitoring yet still provides the patient with a low-cost in home implementation.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

What is claimed:

1. A low-cost, medical image snap-shot formatting device, comprising:

an operations system;

a remote installation;

a camera; and a non-camera peripheral;

wherein the operations system comprises an image processing circuit and a videophone, the image processing circuit comprising a first digital signal processor operably coupled to a first signal formatting component, the first digital signal processor operating under control of a first pre-determined program and a second digital signal processor operating under control of a second pre-determined program, said second digital signal processor operably coupled to said first digital signal processor, wherein said first signal formatting component is capable of receiving medical image snap-shot data from the camera and, wherein upon said first signal formatting component receiving said medical image snap-shot data, the first signal digital signal processor formats said medical image snap-shot data into a digital format, if said medical image snap-shot data is not already in a digital format, and supplies the digitally formatted medical image data to said second digital signal processor in both a first thumbnail image suitable for transfer over a plain old telephone system and a second high-resolution snap-shot image suitable for transfer over a plain old telephone system;

wherein said second digital signal processor supplies the first thumbnail image to the videophone wherein a videophone processor transmits the first thumbnail image to the remote installation over the plain old telephone system and wherein the second digital processor stores the second high-resolution snap-shot image in an image memory;

wherein the remote installation comprises a video display and a communication device whereupon said remote installation receives and displays said first thumbnail image and wherein said communication device communicates over the plain old telephone system to selectively request transmission of the second high-resolution image or the taking of a new medical image with the camera.

2. The device of claim 1, wherein said first thumbnail image is compressed to a range of 90%–99% of said high-resolution snap-shot image.

3. The device of claim 1, wherein said medical image snap-shot data is in a format selected from a group consisting of: USB, S-video, and composite video.

4. The device of claim 1, wherein said device is implemented within a patient system of a telemedicine system.

5. The device of claim 1, further comprising a synchronizing device that is operably coupled intermediate said first digital signal processor and said first signal formatting component.

6. The device of claim 5, wherein said synchronizing device comprises a field programmable gate array.

7. The device of claim 1, further comprising a second signal formatting component wherein said second signal formatting component receives said medical image snap-shot data and formats said medical image snap-shot data into an NTSC format, if said medical image snap-shot data is not already in said NTSC format.

8. The device of claim 1, wherein said first digital signal processor compresses according to an adjustable compression loss percentage.

* * * * *